United States Patent [19]

Brodsky et al.

[11] Patent Number: 5,129,391
[45] Date of Patent: Jul. 14, 1992

[54] THERMAL PACKS

[75] Inventors: James M. Brodsky, Villa Park; Randy A. Evans, Redondo Beach, both of Calif.

[73] Assignee: M.S.C.M., Inc., Villa Park, Calif.

[21] Appl. No.: 500,928

[22] Filed: Mar. 29, 1990

[51] Int. Cl.$^5$ ............................................. A61F 7/00
[52] U.S. Cl. ................................. 128/380; 128/402; 128/403; 128/379
[58] Field of Search .................... 128/394–403, 128/379, 380; 62/530; 623/8

[56] References Cited

U.S. PATENT DOCUMENTS

| | | | |
|---|---|---|---|
| 3,463,161 | 8/1969 | Andrassy | 128/402 |
| 3,871,376 | 3/1975 | Kozak | 128/403 |
| 3,986,213 | 10/1976 | Lynch | 613/8 |
| 4,324,111 | 4/1982 | Edwards | 62/530 |
| 4,596,250 | 6/1986 | Beisang, III et al. | 128/423 |
| 4,753,240 | 6/1988 | Sparks | 128/379 |
| 4,765,338 | 8/1988 | Turner | 128/402 |

Primary Examiner—William H. Grieb
Assistant Examiner—Mark S. Graham
Attorney, Agent, or Firm—G. Donald Weber, Jr.

[57] ABSTRACT

A CRYLON ™ gel containing glass beads and a light metal, formulated to be pliable when frozen, yet reusable and stable enough to permit repeated thawing and freezing, is contained within a vinyl package having a covering which is both hypoallergenic and waterproof. The packages are comfortably held in place, e.g. pressed against an injured portion of the body, by appropriate straps and/or fasteners, which may form a part of the package.

18 Claims, 2 Drawing Sheets

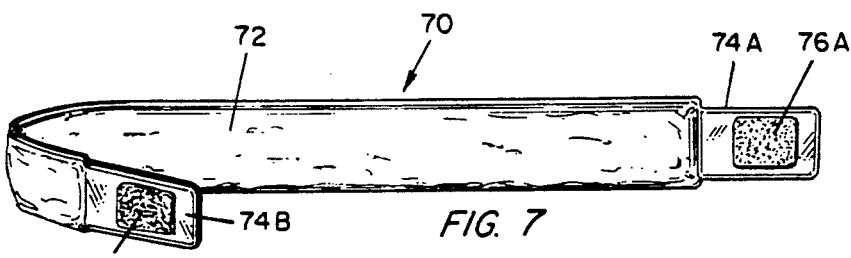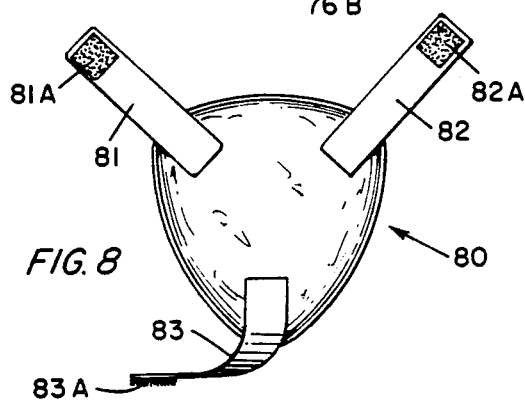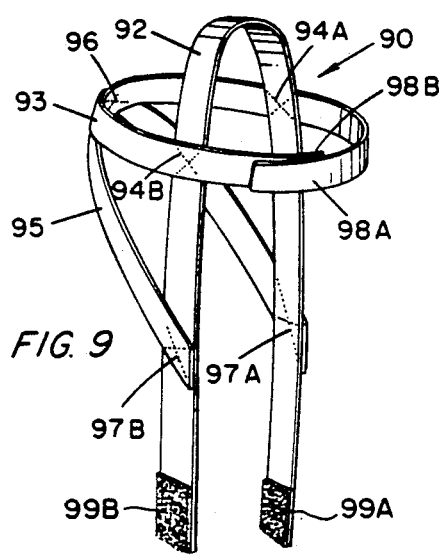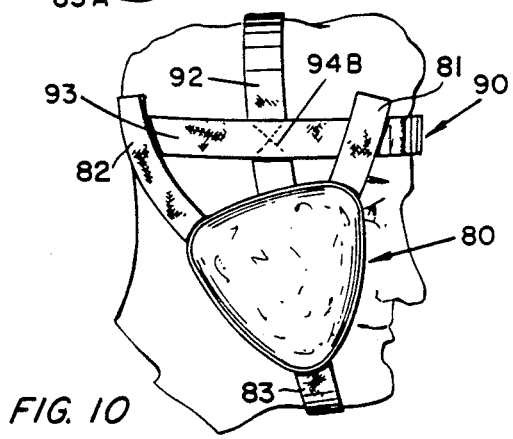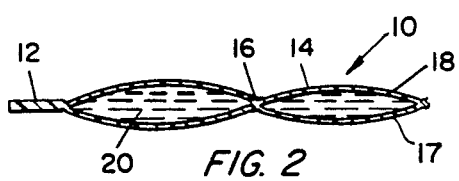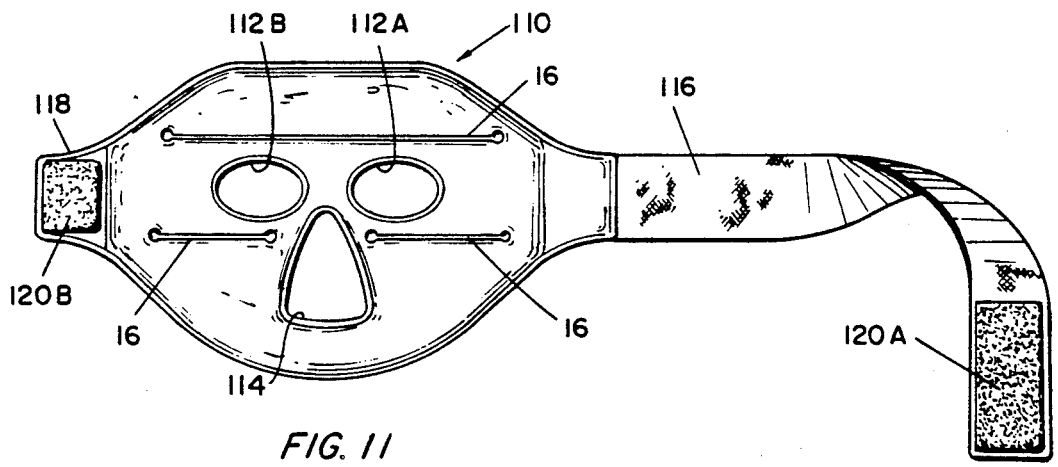

THERMAL PACKS

BACKGROUND

1. Field of the Invention

This invention relates, generally, to "cold packs" used to treat a variety of injuries. More specifically, the invention provides a novel, reusable, stable, nontoxic and freezable gel contained within uniquely shaped packages formed of hypoallergenic materials which are held in place by straps and/or fasteners.

2. Prior Art

Cold packs have gradually been evolving from the most primitive form, i.e. ice cubes wrapped within some toweling, to more sophisticated, reusable forms. The ice-cube-in-toweling type of cold pack has well-known drawbacks. For example, the ice cubes melt and the toweling becomes soaked. This, in turn, soaks the user and the surrounding area.

There is also the fatigue factor which sets in after the user holds the ice cube bundle against the injury for an extended period of time Sometimes this procedure further aggravates the situation by causing both the hand and the injury to become numbed by the cold.

Ice cubes are not comfortable because they are hard and often have sharp points or edges which may cause additional discomfort. The shape of ice cubes themselves makes it inherently difficult to press them against an injured area. This all presupposes that ice cubes are even available.

Frozen packaged water is an improvement because, as the water melts, it is retained within the package. It is relatively easy to keep the package in the freezer until needed. The packages are, generally, cubic or rectilinear in shape, so that much of the discomfort and effort of prior art devices remain although some convenience is gained.

More recently, the material providing the "cold" may be a variety of chemical mixtures. One mixture is the basic "freeze-and-use" kind which is better than water only because it stays cold longer. This material is commonly referred to as Blue Ice. Nevertheless, it is still as hard and uncomfortable as the prior art ice packs.

Other chemical mixtures used to provide the "cold" are more pliable when frozen or when absorbing heat (as in those which involve endothermic reactions), but the packaging is uncomfortable and must be manually held against the injury. Thus, the fatigue of the holder and discomfort from the packaging is not resolved even if the chemical mixture is improved. Moreover, some of the prior art devices are considered to be toxic if broken.

Other attempts to provide a cold pack to deal with these problems have resulted only in partial and inadequate remedies. The invention described herein provides a reasonably comfortable and useful thermal pack which contours against injured areas without the necessity of manual holding. The cold producing mixture (i.e. CRYLON (TM) gel) of the thermal pack is a unique and effective mixture.

PRIOR ART STATEMENT

Applicant has made no formal search of the prior art. However, the best known prior art is described above.

SUMMARY OF THE INSTANT INVENTION

The thermal pack of the instant invention includes a specially formulated chemical mixture composed of water, an electolyte, a cellulose collosize resin, glass microspheres, and a light metal such as titanium oxide. This chemical mixture, referred to as CRYLON (TM) gel, may be repeatedly frozen and thawed without dissipating the capacity of the gel to provide cold relief to an injury. Furthermore, this gel has the significant characteristics of being non-toxic; being pliable while frozen; having a greater capacity to remain cold; being relatively easy and inexpensive to produce, and so forth.

The novel CRYLON (TM) gel is contained within packages made of a pliable, hypoallergenic material such as EMKST Blue Mat vinyl or MF150 medical grade vinyl. The package retains the gel without seepage and does not irritate even sensitive skin. The packages have contoured shapes which allow the benefits of the cold gel to be comfortably available to even awkward places on the body. The packages are held in place by a variety of straps and/or fasteners, usually of the hook-and-loop type.

BRIEF DESCRIPTION OF THE DRAWINGS

FIG. 2 is a truncated cross-sectional view taken along the lines 2—2 of the representative panel shown in FIG. 1.

FIG. 7 is an isometric view of another embodiment of the invention to be used on cylindrical shaped parts of the body.

FIG. 8 is a plan view of part of another embodiment of the invention which is a multi-purpose patch.

FIG. 9 is an isometric view of a support assembly for the patch embodiment of the invention as shown in FIG. 8.

FIG. 10 is a side view of the invention wherein the separate parts shown in FIGS. 8 and 9 are combined.

FIG. 11 is a plan view of another embodiment of the instant invention which is shaped to conform to the face.

DESCRIPTION OF PREFERRED EMBODIMENTS

Figure 1:
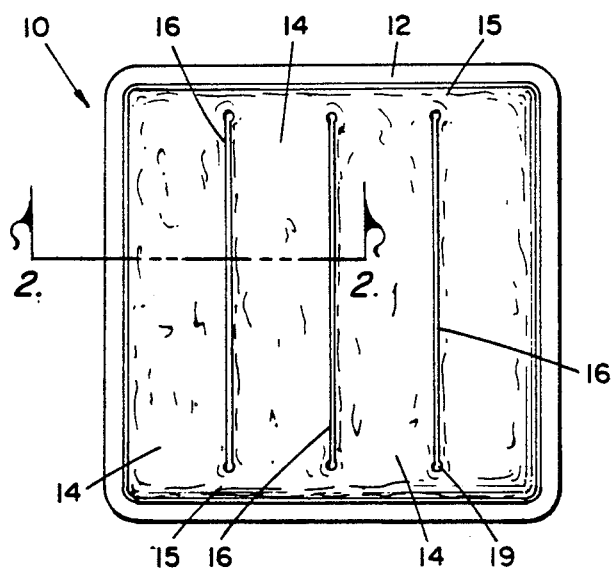
FIG. 1 is a plan view of a panel which is representative of on embodiment of the instant invention.

Referring now to FIGS. 1 and 2 concurrently, there is shown one embodiment of instant invention. This embodiment takes the form of a panel-type pack. The representative panel 10 has a peripheral seal 12 which surrounds the entire panel 10 and acts to retain the gel 20 within the panel 10 The peripheral seal 12 can take the form of lips or a brim which forms a border around the outer edge of the panel 10. In practice, the seal 12 is formed by joining together the edges of an upper layer 14 and a lower layer 17. These layers form the upper and lower surfaces of the panel 10. While two joined together layers are preferred, a single piece of material may be folded over on itself and sealed around the perimeter thereof.

The panel 10 is formed of at least one layer of material which is pliable, hypoallergenic and completely resistant to seepage of the gel 20. Furthermore, the material (and the peripheral seal) is leakproof, and is not affected by temperature changes over a wide range, for example from $-10°$ to $\pm150°$ F. The material used in this panel 10 is, typically, EMKST or MF150 type vinyl or the like. Of course, other suitable materials are contemplated.

The panel 10 has a plurality of pockets 14 which are created by internal baffle seams 16 within the panel 10. The baffle seams 16 are formed by joining the upper and lower layers together in a suitable fashion.

Typically, the seams 16 are spaced apart and substantially parallel to each other. However, other arrangements can be provided in order to establish suitable pack configuration and conformability. Between the baffle seams, a plurality of parallel, columns of gel are provided The baffle seams 16 insure that the gel 20 will not "bunch up" and accumulate in one location within the panel 10. The baffle seams 16 do not extend from the inner edge of seal 12 on one side of the panel seal 12 to the inner edge of seal 12 on the opposite side. Thus, a small space 15 is provided between the seam 16 and the seal 12 wherein a limited amount of gel movement is permitted within the panel, thereby providing some internal "give" in the panel 10.

In the preferred embodiment, the outer seal 12 and baffle seams 16 are formed by ultrasonic or RF welding techniques. Of course, a seal can be produced by a heat and pressure process. Alternatively, the layers may be glued, tacked by laser welding, or joined together by other methods appropriate to the material used.

The gel 20 of the instant invention is a reusable, cryogenic formulation which is known as CRYLON (TM) gel. This gel 20 has a unique formula containing water, sodium chloride, hydroxyethyl cellulose collosize resin, titanium dioxide, and glass microspheres.

A preferred formula for the gel used in the Cold Pack is of the form $(T_1O_2+Al_2O_3+SiO_2)(H_2O+NaCL)<<C_6H_9O_5><C_2H_4O>xH>_n$ (1/32 3080 MICROGLASS TM spheres). More generally, the CRYLON gel includes an insoluble, colloidal, homogenized emulsion made up of one or more light metals, such as titanium dioxide, alumina trioxide, or the like, together with silica dioxide and MICROGLASS TM spheres, dispersed in a slurry of air and 2-hydroxyethyl-ether (or 2-hydroxyethyl-methyl) cellulose.

Figure 12:
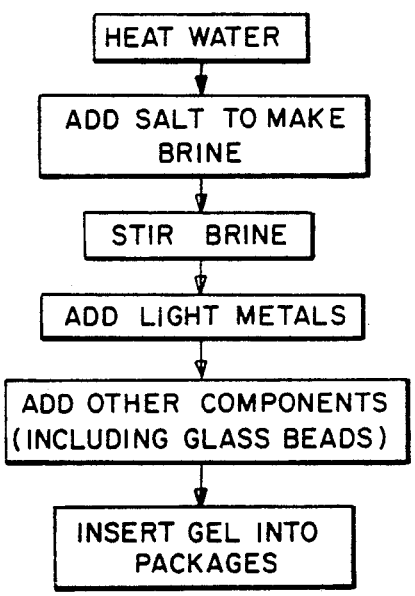
FIG. 12 is a block diagram of the process used in making the unique gel used in these products.

The process used in preparing the gel includes a plurality of steps, as shown in FIG. 12, as enumerated herewith.

Step One: A support medium of 40 to 80 gallons of water is heated to a temperature of about 80° to 120° F.

Step Two: A brine slurry is formed by adding about 140 to 180 pounds of kiln-dried, water softening salt or equivalent to the warm water.

Step Three: The brine is mixed and stirred for about 15 to 60 minutes in order to make a uniform, homogeneous slurry. The mixing rate can be varied and/or controlled, as desired.

Step Four: While mixing, various components are added to the brine. Typically, the components include:
1.3 oz. to 160.4 oz. of titanium dioxide;
0.05 oz. to 12.6 oz. of alumina trioxide; and
6.2 oz. to 94.4 oz. of silica dioxide Mixing of this combination of ingredients continues for about 5 to 10 minutes, as required.

Step Five: While continuing the mixing or stirring, additional materials are added to the mixture. For example,
22.6 oz. to 259.8 oz. of 2-hydroxyethyl-ether cellulose;
1.63 oz. to 28.4 oz. of sodium acetate;
0.82 oz. to 9.42 oz. of unreacted cellulose;
0.02 oz. to 6.26 oz. of glyoxal; and
164.6 oz. to 289.2 oz. of 1/32 (3080) MICROGLASS TM spheres.

After these materials are added, mixing continues for about 10 to 20 minutes at about 50° to 150° F., depending upon the speed of mixing, the viscosity the mixture and so forth.

Step Six: The gel is then placed within the panel (or pouch) which has been formed in the desired configuration, as shown and described herein.

Even when frozen or cooled to low temperatures, the gel 20 is plastic and pliable as is the vinyl material which is used to form panel 10. This characteristic provides a relatively "soft" thermal pack (referred to as a trademark or a COLD BRACE TM) which can readily conform to the shape of the appropriate body area. For example, the pattern of the baffle seams 16 is arranged to permit the panel 10 to be conformed to accommodate specific areas of the body.

Figure 3:
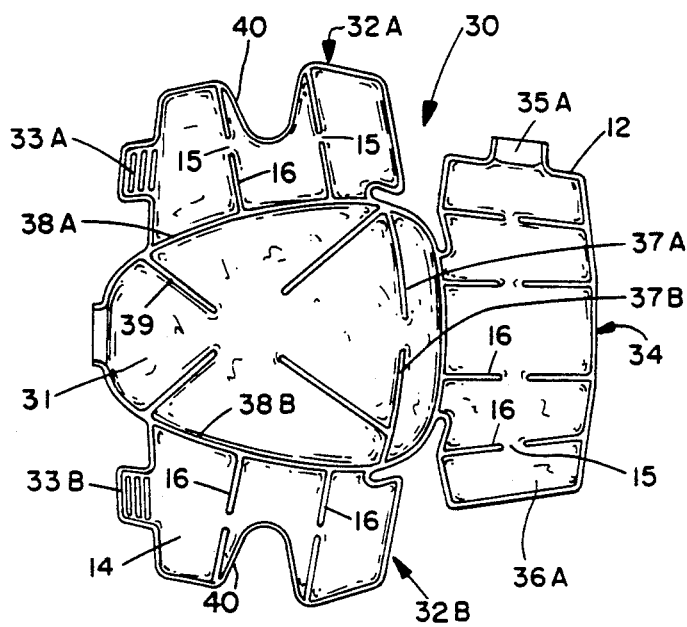
FIG. 3 is a plan view of another embodiment of the instant invention which is contoured for use on the head.
Figure 4:
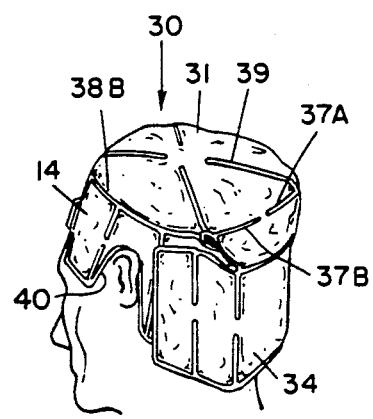
FIG. 4 is an isometric view of the embodiment of the invention shown in FIG. 3 when in use on the head of a person.

Referring now to FIGS. 3 and 4 concurrently, there is shown another embodiment of the instant invention. In this embodiment, the basic construction of the representative panel 10 as shown in FIGS. 1 and 2 is utilized to produce a thermal pack which is contoured into a head pack 30. The head pack 30 has a panel 31 which is somewhat oval in shape. Panel 31 is contoured to approximately cover the top or upper area of the head of the user. Lateral flaps 32A and 32B extend from opposite sides of panel 31. The flaps are shaped to cover the temporal portion of the head. In a preferred embodiment, flaps 32A and 32B include openings 40 so that the ears of the wearer are not covered. Tabs 33A and 33B, respectively, extend from a side of the lateral flaps 32A and 32B. In use, the flaps 32A and 32B are folded downwardly whereby the tabs 33A and 33B overlap in front at the forehead. The tabs are held together by a suitable fastener. In this embodiment, hook and loop fasteners (frequently sold under the registered trademark Velcro) are used. However fasteners such as snaps, strings or the like are also contemplated.

A rear flap 34 extends from the back of the panel 31. Rear flap 34 is shaped to cover the posterior of the head from the back edge of the lateral flaps 32A and 32B to the occipital area of the skull. The rear flap 34 includes fasteners at the edges thereof. The fasteners may take the form of a tab extension 35A or section 36A thereof. The tab 35A or section 36A overlap a portion of the lateral flaps 32A and 32B. The rear flap fasteners 35A and 36A can be of any suitable design although hook-and-loop fasteners are preferred.

The lateral and rear flaps can be separate gel packs which are joined to panel 31 by common borders. Alternatively, some or all of the flaps and panels can be integrally joined and capable of exchange of gel materials.

The baffle seams 16 of this embodiment provide additional contouring flexibility to allow greater comfort to the wearer and a closer conformance between the head pack 30 and the body areas. A pair of posterior baffle seams 37A and 37B in panel 31 permit the rear flap 34 to enclose the back portion of the head more snugly. Seams 38A and 38B are positioned to provide a fold line thereby allowing the lateral flaps 32A and 32B to more easily articulate downwardly from the panel 31. Seams 38A and 38B may be edge seams between separate segments of the "cranial pack" 30 or they may be baffle seams as noted above.

To provide additional comfort and a better fit, the panel 31 has a pattern of baffle seams 39 which allows the pack to mold about the upper portion of the head. The plurality of vertical baffle seams 16 permit the lateral flap 32A and 32B and the rear flaps 34 to closely encase the circumference of the head. Of course, the pattern of the baffle seams may be varied to permit the pack 30 to snugly enclose the head.

FIG. 4 particularly shows how the baffle seams, the contouring of the panel and flaps, and the fasteners conform the head pack 30 to head of an individual. It is seen that the pack 30 covers a substantial portion of the user's head without covering the wearer's ears.

Figure 5:
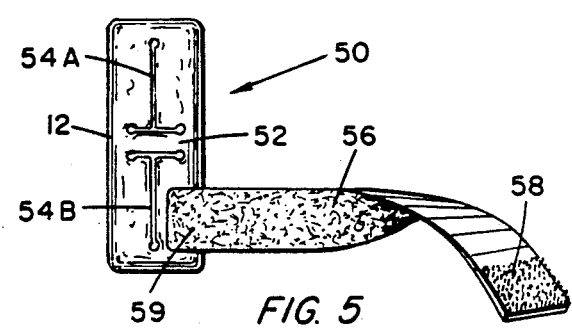
FIG. 5 is a plan view of another embodiment of the instant invention which is formed and sized for use on the digits.
Figure 6:
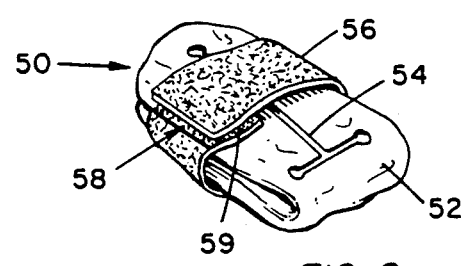
FIG. 6 is an isometric view of the embodiment of the invention shown in FIG. 5 which is folded as it would be when in use.

Referring now to FIGS. 5 and 6 concurrently, there is shown another embodiment of the instant invention. In this embodiment, the panel 10 shown in FIGS. 1 and 2 is contoured into a "digit pack" 50. Typically, the panel 50 is rectangular in shape with one plan dimension greater than the other. The baffle seams 54A and 54B are each T-shaped. The cross-bars of the T-shaped seams are adjacent and parallel to each other to create a broad fold area 52 therebetween. The broad fold area 52 allows for comfortable accomodation of the digits (i.e. fingers or toes) or an appendage, such as a hand or foot. An elongated strap 56 has one end thereof attached to the pack 50 adjacent an end thereof and, typically, on the exterior of the pack 50. A fastener 58 is provided at the unattached end of the strap 56. Fastener 58 selectively joins with the pack 50 or the attached end of strap 56. For example, fastener 58 and counterpart fastener 59 can be hook-and-loop devices affixed to the strap 56.

In use, the pack 50 is folded over the injured area as shown in FIG. 6. The cross-bars of seams 54A and 54B define the broad fold area 52 which permits the pack to fold around the toes, fingers or the like. The strap 56 is then folded or wrapped around the pack 50 until the fasteners 58 and 59 are connected to thereby hold the pack 50 gently and securely against the injured area.

Referring now to FIG. 7, there is shown another embodiment of the instant invention. In this embodiment, the panel 70 (constructed similarly to the representative panel 10 shown in FIGS. 1 and 2) is relatively long and narrow. Panel 70 is contoured to fit around cylindrically shaped portions of the body such as the torso or limbs (e.g. forearms, thighs, or the like). For convenience, this embodiment is called a torso pack 70 because of its length. The length of panel 70 can be varied as a function of the circumference of the body segments to be treated.

In the torso pack 70 only one pocket 72 is shown. Of course, multiple baffles (or baffle seams) may be used to cover a broader area. Alternatively, several of the packs may be applied adjacent to one another to provide a wider area of coverage. Opposite ends of the torso pack 70 have tabs 74A and 74B, respectively, which extend from the pack. Typically, these tabs are formed of the external packaging material (i.e. vinyl layers) and do not enclose any gel therein. Fasteners 76A and 76B are, respectively, positioned on the tabs 74A and 74B. The fasteners (e.g. hook-and-loop) are engaged to secure the torso pack 70 in place.

Referring now to FIG. 8, there is shown another embodiment of the instant invention. In this embodiment, a patch pack 80 to fit localized areas of injury is provided. The patch pack 80 is provided in similar fashion to the representative panel 10 shown and described relative to FIGS. 1 and 2. As shown, patch pack 80 has a generally triangular shape, but other shapes such as oval, circular, and the like are contemplated. The patch pack 80 includes the exterior package and the improved gel of the invention. The patch pack 80 may vary widely as to size so that coverage is as small as a cheek or as large as the abdomen, for instance. A plurality of tabs 81, 82 and 83 extend from the corners of the patch 80. Typically, the tabs are placed upon the exterior surface of the panel 80. In addition, suitable fasteners 81A, 82A and 83A are provided on the respective tabs. The tabs and fasteners are adapted to be used in conjunction with a variety of securing systems, especially the mounting system (or holding device) shown in FIG. 9.

Referring now to FIG. 9, there is shown the holding device 90. The holding device 90 includes an elongated longitudinal strap 92 which is adapted to snugly enclose the head from the upper surface to below the chin. An elongated lateral strap 93 is mounted to the longitudinal strap 92 at temporal junctions 94A and 94B which are located near the temple of the head holding device 90 when in place. The lateral strap 93 is arranged approximately perpendicular to the longitudinal strap 92 and is adapted to encircle the head, in particular, around the forehead and back of head. Transverse strap 95 is mounted at or near the back of lateral strap 93 at back junction 96. The ends of the transverse strap 95 extend downwardly at an approximately 45° angle to join the longitudinal strap 92 at cheek junctions 97A and 97B. The cheek junctions are located intermediate the temporal junctions and the ends of the longitudinal strap 92. The transverse strap 95 assists in securing the position of the longitudinal strap 92 and lateral strap 93 as well as to further support the panel 80 shown in FIG. 8.

The holding device 90 is selectively closed about the head by means of two sets of fasteners 98A and 98B, and 99A and 99B, respectively. Fasteners 98A and 98B are located at the forehead side of the lateral strap 93. Typically, the fasteners comprise hook-and-loop devices at the ends of the strap 96. Similarly, fasteners 99A and 99B are positioned beneath the chin on longitudinal strap 92. Also, these fasteners comprise hook-and-loop devices at the ends of the strap 92. The placement of these fasteners and the straps of the holding device 90 (in the form of a head gear) may vary in position and angle so long as a comfortable apparatus is formed to both accomodate the wearer and secure any panel patch, in particular, the panel 80.

The several straps 92, 95 and 96 (or all of them) may include pockets for retaining gel therein (similar to the torso pack 70 shown in FIG. 7). Conversely, the straps may be relatively thin, flat strips of vinyl (or similar material) which are used only as a support mechanism for panel 80 type devices.

Referring now to FIG. 10, there is shown another embodiment of the instant invention. In this embodiment, a panel 80 as shown in FIG. 8, sized and contoured to fit on the cheek, is shown with holding device 90 as in FIG. 9. In particular, the fasteners 81A, 82A and 83A on tabs 81, 82 and 83, respectively, are joined to the straps 92, 96 and/or 95. This arrangement causes panel 80 to be secured to the head gear holding device 90. By adjusting the position of the panel 80, treatment can be applied to the wearer's cheek, eye, chin, jaw, ear or assorted head locations. With this arrangement a number of panels 80 can be substituted for each other in order to provide a substantially constant cold treatment with a single headgear holding device.

Referring now to FIG. 11, there is shown another embodiment of the instant invention. In this embodiment, face pack 110 is fabricated similar to the representative panel 10 shown in FIGS. 1 and 2. The face pack 110 is contoured to engage the face of a wearer. For example, the pack 110 has eye openings 112A and 112B and nose opening 114 therethrough to accomodate the physiognomy of a wearer. This embodiment includes a strap 116 on one side of the face pack 110 and a tab 118 on the opposite side. Fasteners 120A and 120B are provided on the strap 116 and tab 118 respectively in appropriate positions to permit the securing of the face pack 110 to the wearer.

It should be understood that illustrative fastener designs are provided. For example, strap 116 and tab 118 are shown on the face pack 110 in FIG. 11. A pair of tabs 74A and 74B are shown on the torso pack 70 in FIG. 7. A single strap 56 is shown on the digit pack 50 in FIGS. 5 and 6. A series of tabs is shown on the head pack 30 in FIGS. 3 and 4. Thus, each shape of thermal pack may use a different combinations of tabs and straps. The straps may be an entirely separate piece which meshes with the fasteners on the particular pack. The fasteners shown are of the hook-and-loop type, but may be snaps, latches, or other suitable closure mechanisms. The straps may use D-rings, snaps, resilient material, or the like to secure the thermal pack in place.

The attachment of the straps and fasteners to the thermal packs are appropriate to the material used. The means of attachment is by stitching, gluing, thermal fusion, ultrasonic welding, RF sealing and other methods.

The tabs and straps seen in the embodiments are, generally, produced of the thermal pack vinyl material. Of course, the tabs could be formed from other materials which may be attached to the main body of the pack by similar methods as are used with the straps and fasteners.

Thus, there is shown and described a unique design and concept of a thermal packs and cryogenic gel. A particular formulation of gel is shown and described herein. Likewise, a variety of pack configurations is shown and described, as well. While this description is directed to particular embodiments, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

We claim:

1. A thermal pack comprising,
a package formed of first and second layers, each formed of a pliant, liquid impervious material,
said first and second layers joined together by a peripheral seal,
said package is configured to engage selected exterior areas of the human anatomy, and
a gel material retained within said package,
said gel comprising an insoluble, colloidal, homogeneous emulsion including at least one light metal and a plurality of glass beads dispersed in a cellulose material.

2. The thermal pack recited in claim 1 wherein,
said package includes at least one internal seal formed between said first and second layers of said material and within said peripheral seal.

3. The thermal pack recited in claim 1 wherein,
said liquid impervious material comprises a vinyl.

4. The thermal pack recited in claim 1 wherein,
said glass beads are hollow glass spheres.

5. The thermal pack recited in claim 1 wherein,
said light metal is at least one of the class comprising titanium, aluminum, silicon, as well as oxides thereof.

6. The thermal pack recited in claim 1 wherein,
said cellulose material includes at least one of a hydroxyethyl-ether and hydroxyethyl--methyl material.

7. The thermal pack recited in claim 1 including,
fastener means extending from said package and adapted to secure at least portions of said package in an operable position.

8. The thermal pack recited in claim 1 wherein,
said package includes a plurality of internal seals between said first and second layers of material,
said plurality of internal seals are substantially parallel to each other.

9. The thermal pack recited in claim 1 wherein,
said package includes a plurality of internal seals between said first and second layers of material,
said plurality of internal seals are arranged at an angle to each other.

10. The thermal pack recited in claim 1 wherein,
said gel material comprises water, sodium chloride, hydroxyethel cellulose resin, and titanium dioxide, and said heads comprise glass microspheres.

11. The thermal pack recited in claim 1 wherein,
said package includes a pair of T-shaped internal seals with the cross-bar of said T-shaped seals in adjacent, parallel arrangement.

12. The thermal pack recited in claim 1 including,
mounting means adapted to be worn by a user of the pack,
said mounting means including joinder means adapted to join said package to said mounting means.

13. The thermal pack recited in claim 1 wherein,
said package includes at least one aperture therethrough to accomodate a portion of the wearer's anatomy.

14. The thermal pack recited in claim 3 wherein,
said package includes a plurality of interconnected pockets.

15. The thermal pack recited in claim 14 wherein,
said pockets are interconnected so that said gel material can flow from one packet to another.

16. The thermal pack recited in claim 14 wherein,
said plurality of pockets includes a first pocket in the form of a relatively planar pocket adapted to conform to the top of the head of the user, and
at least three depending pockets which are joined to edges of said first pocket and adapted to depend therefrom thereby to conform to the sides of the head of the user.

17. The thermal pack recited in claim 16 including,
fastener means for joining said three depending pockets together to form a continuous pocket wall.

18. The thermal pack recited in claim 12 wherein,
said package has a generally triangular configuration.

* * * * *